(12) United States Patent
Ogura et al.

(10) Patent No.: US 6,793,628 B2
(45) Date of Patent: Sep. 21, 2004

(54) BLOOD-PRESSURE MEASURING APPARATUS HAVING AUGMENTATION-INDEX DETERMINING FUNCTION

(75) Inventors: Toshihiko Ogura, Komaki (JP); Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 86 days.

(21) Appl. No.: 10/351,546

(22) Filed: Jan. 27, 2003

(65) Prior Publication Data

US 2003/0199774 A1 Oct. 23, 2003

(30) Foreign Application Priority Data

Apr. 17, 2002 (JP) ...................................... 2002-115185

(51) Int. Cl.[7] .............................................. A61B 5/02
(52) U.S. Cl. ..................................... 600/490; 600/494
(58) Field of Search ........................ 600/490, 492–496, 600/500–503, 485

(56) References Cited

U.S. PATENT DOCUMENTS 5,265,011 A  11/1993 O'Rourke
6,612,993 B2 * 9/2003 Narimatsu .................. 600/500

FOREIGN PATENT DOCUMENTS

EP  0 655 219 A1  5/1995
EP  1 340 453 A2  9/2003

* cited by examiner

*Primary Examiner*—Mary Beth Jones
*Assistant Examiner*—Navin Natnithithadha
(74) *Attorney, Agent, or Firm*—Oliff & Berridge, PLC

(57) ABSTRACT

A blood-pressure measuring apparatus including a cuff which is adapted to be worn on a portion of a living subject to press the portion, an augmentation-index determining device for determining an augmentation index of the subject based on a cuff pulse wave obtained from the cuff, and a cuff-pulse-wave obtaining device for obtaining, during a pressing period in which the cuff presses the portion of the subject for measuring a blood pressure of the subject, the cuff pulse wave from the cuff so that the augmentation-index determining device determines the augmentation index based on the obtained cuff pulse wave.

5 Claims, 7 Drawing Sheets

BLOOD-PRESSURE MEASURING APPARATUS HAVING AUGMENTATION-INDEX DETERMINING FUNCTION

BACKGROUND OF THE INVENTION

1. Field of the Invention

The present invention relates to a blood-pressure measuring apparatus having the function of determining an augmentation index based on a cuff pulse wave occurring to a cuff worn on a living subject.

2. Related Art Statement

Augmentation index, generally known as AI, indicates, e.g., a proportion of a reflected-wave component of a pulse wave to an incident-wave component of the same, and is used to evaluate compliance of aorta. As the compliance of aorta increases, the reflected-wave component decreases and, as the compliance of aorta decreases, the reflected-wave component increases. More specifically described, if wall of aorta hardens, a reflected-wave component contained in the form of pulse wave obtained from the aorta increases. Thus, augmentation index reflects arteriosclerosis, and can be used as an index for inspecting arteriosclerosis.

As described above, augmentation index indicates a proportion of a reflected-wave component of a pulse wave to an incident-wave component of the same, but it is difficult to separate a pulse wave detected (hereinafter, referred to as a detected pulse wave) into its incident-wave component and reflected-wave component. Hence, an augmentation index may be determined as follows: First, a detected pulse wave is analyzed to identify respective peak points of an incident-wave component and a reflected-wave component of the pulse wave. Then, the augmentation index is calculated by dividing a difference between a magnitude of the pulse wave at the time of occurrence of the peak of the incident-wave component and a magnitude of the pulse wave at the time of occurrence of the peak of the reflected-wave component, by a pulse pressure of the pulse wave. In addition, the peak of the incident-wave component may be determined as an inflection point or a local maximum point between a rising point of the detected pulse wave and a peak of the same; and the peak of the reflected-wave component may be determined as the first local maximum point following the peak of the incident-wave component.

Since augmentation index is used to evaluate compliance of aorta as described above, it is a clinical practice to non-invasively detect a pulse wave from a carotid artery that is the nearest to the aorta and determine an augmentation index based on the carotid pulse wave. However, first, it needs adequate skill to wear, at an appropriate position, a carotid-pulse-wave sensor for detecting a carotid pulse wave and, second, it is needed to use or employ the carotid-pulse-wave sensor. Thus, there is a need to easily measure an augmentation index using a cuff pulse wave which is detected from a cuff worn on, e.g., an upper arm of a living subject for measuring a blood pressure of the subject.

Here, it may be possible to provide a blood-pressure measuring apparatus which measures a blood pressure using a cuff and which has the function of determining an augmentation index based on a cuff pulse wave occurring to the cuff. However, when the blood-pressure measuring apparatus having the augmentation-index determining function is used to measure a blood pressure and an augmentation index, it takes not only a pulse-wave detection time needed to keep the cuff pressure at a pulse-wave detection pressure, for detecting a cuff pulse wave to be used to determine the augmentation index, but also a blood-pressure measurement time needed to increase the cuff pressure up to a pressure higher than a systolic blood pressure of a living subject, for pressing a portion of the subject and thereby measuring the blood pressure of the subject. Thus, the subject is pressed by the cuff for an increased time and accordingly feels an increased amount of load.

SUMMARY OF THE INVENTION

It is therefore an object of the present invention to provide a blood-pressure measuring apparatus which has the function of determining an augmentation index and which can measure blood pressure and augmentation index by pressing, with a cuff, a portion of a living subject for a short time.

The above object has been achieved by the present invention according to which there is provided a blood-pressure measuring apparatus comprising a cuff which is adapted to be worn on a portion of a living subject to press the portion; an augmentation-index determining means for determining an augmentation index of the subject based on a cuff pulse wave obtained from the cuff, and a cuff-pulse-wave obtaining means for obtaining, during a pressing period in which the cuff presses the portion of the subject for measuring a blood pressure of the subject, the cuff pulse wave from the cuff so that the augmentation-index determining means determines the augmentation index based on the obtained cuff pulse wave.

According to this invention, during the pressing period in which the cuff presses the portion of the subject for measuring the blood pressure of the subject, the cuff-pulse-wave obtaining means obtains the cuff pulse wave for determining the augmentation index of the subject. Thus, the pressing period in which the cuff presses the portion of the subject for measuring the augmentation index and the blood pressure can be advantageously shortened.

According to a preferred feature of the present invention, the blood-pressure measuring apparatus further comprises a pulse-wave-detection-pressure keeping means for keeping a pressure in the cuff to a pre-determined pulse-wave detection pressure, and the cuff-pulse-wave obtaining means obtains, as the cuff pulse wave, a pressure oscillation occurring to the cuff in a state in which the pressure in the cuff is kept at the pre-determined pulse-wave detection pressure.

According to this feature, in the state in which the pressure of the cuff is kept at the pre-determined pulse-wave detection pressure by the pulse-wave-detection-pressure keeping means, the cuff-pulse-wave obtaining means obtains the cuff pulse wave. Thus, the cuff pulse wave is free from deformation caused by changing of the cuff pressure, and accordingly an accurate augmentation index can be determined based on the cuff pulse wave.

According to another feature of the present invention, the pulse-wave-detection-pressure keeping means keeps the pressure in the cuff to the pre-determined pulse-wave detection pressure, in each of an initial portion and a terminal portion of the pressing period, and the cuff-pulse-wave obtaining means obtains, as a first cuff pulse wave, a pressure oscillation occurring to the cuff in a state in which the pressure in the cuff is kept at the pre-determined pulse-wave detection pressure in the initial portion of the pressing period, and obtains, as a second cuff pulse wave, a pressure oscillation occurring to the cuff in a state in which the pressure in the cuff is kept at the pre-determined pulse-wave detection pressure in the terminal portion of the pressing period, and the augmentation-index determining means determines a first augmentation index of the subject based on the first cuff pulse wave obtained from the cuff in the initial portion of the pressing period, and determines a second augmentation index of the subject based on the second cuff pulse wave obtained from the cuff in the terminal portion of the pressing period.

According to this feature, the augmentation-index determining means determines respective augmentation indexes of the subject based on respective cuff pulse waves obtained in the initial and terminal portions of the pressing period in which the cuff presses the portion of the subject for measuring the blood pressure of the subject.

According to another feature of the present invention, the blood-pressure measuring apparatus further comprises a modified-augmentation-index determining means for determining a modified augmentation index based on the first and second augmentation indexes determined by the augmentation-index determining means.

According to this feature, the modified-augmentation-index determining means determines, based on the respective augmentation indexes determined by the augmentation-index determining means from the respective cuff pulse waves obtained in the initial and terminal portions of the pressing period in which the cuff presses the portion of the subject for measuring the blood pressure of the subject, the modified augmentation index freed from influences caused by the deformation of skin and subcutaneous tissue of the subject's portion that contain a lot of water.

According to another feature of the present invention, the blood-pressure measuring apparatus further comprises an artery evaluating means for evaluating a degree of arteriosclerosis or a vascular endothelium of the subject based on the first and second augmentation indexes determined by the augmentation-index determining means.

For example, the artery evaluating means compares the respective cuff pulse waves, or the respective augmentation indexes, obtained in the initial and terminal portions of the pressing period, with each other, and evaluates a degree of softness of arteries of the subject based on a difference of respective amplitudes of the two cuff pulse waves, a difference of respective areas of the two cuff pulse waves, or a difference of the two augmentation indexes. In this case, as the amplitude difference of the two cuff pulse waves, the area difference of the two cuff pulse waves, or the difference of the two augmentation indexes increases, the degree of softness of arteries increases; and as the amplitude difference, the area difference or the augmentation-index difference decreases, the degree of arteriosclerosis or the degree of hardness of vascular endothelium increases.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
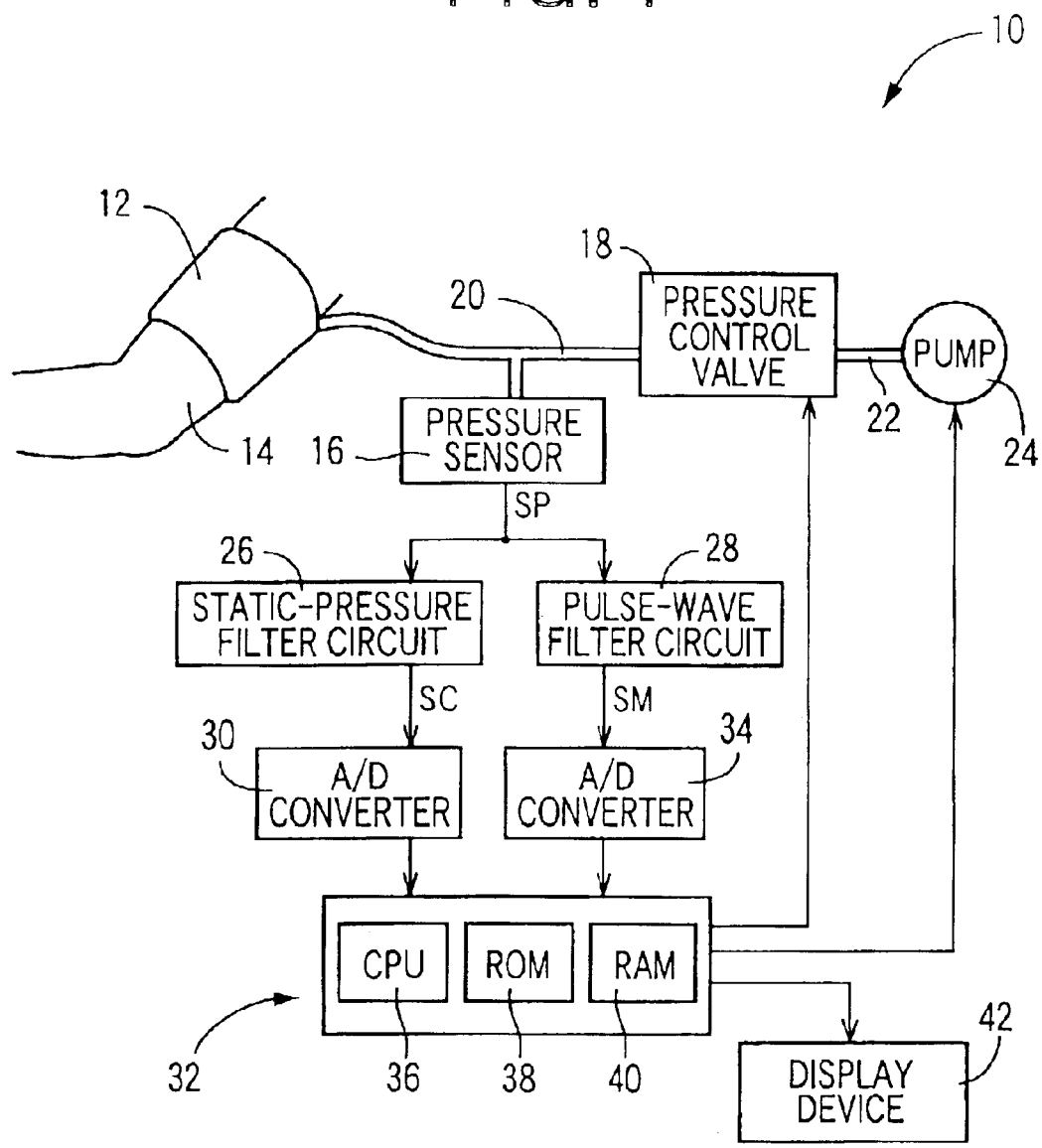
FIG. 1 is a diagrammatic view showing a circuitry of a blood-pressure measuring apparatus which has an augmentation-index determining function and to which the present invention is applied.

Hereinafter, there will be described an embodiment of the present invention in detail by reference to the drawings. FIG. 1 is a diagrammatic view showing a circuitry of a blood-pressure measuring apparatus 10 to which the present invention is applied and which has an augmentation-index measuring function. The present blood-pressure measuring apparatus 10 can also be used as an arteriosclerosis inspecting apparatus.

In FIG. 1, reference numeral 12 designates an inflatable cuff which includes a belt-like cloth bag and a rubber bag accommodated in the cloth bag and which is adapted to be wound around an upper portion 14 of a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit (i.e., a pulse-wave filter device) 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, Pc). The filter circuit 26 supplies the cuff-pressure signal SC to an electronic control device 32 via an A/D (analog-to-digital) converter 30. The pulse-wave filter circuit 28 includes a band-pass filter that permits passing of signals having frequencies of from 1 to 30 Hz and thereby extracts, from the pressure signal SP, a cuff-pulse-wave signal, SM, representing a cuff pulse wave as an oscillatory component of the detected air pressure. The filter circuit 28 supplies the cuff-pulse-wave signal SM to the control device 32 via an A/D converter 34. The cuff pulse wave represented by the cuff-pulse-wave signal SM is a pressure oscillation transmitted from an artery of the subject to the cuff 12 and, since this artery is a brachial artery, the cuff pulse wave is a brachial pulse wave.

The control device 32 is provided by a so-called microcomputer including a CPU (central processing unit) 36, a ROM (read only memory) 38, a RAM (random access memory) 40, and an I/O (input-and-output) port, not shown. The CPU 36 processes signals according to the control programs pre-stored in the ROM 38 by utilizing the temporary-storage function of the RAM 40, and supplies drive signals via the I/O port to the air pump 24 and the pressure control valve 18 so as to control the cuff pressure Pc. Moreover, the CPU 36 has various functions shown in detail in FIG. 2 for determining an augmentation index AI of the subject, and controls what is displayed by a display device 42.

Figure 2:
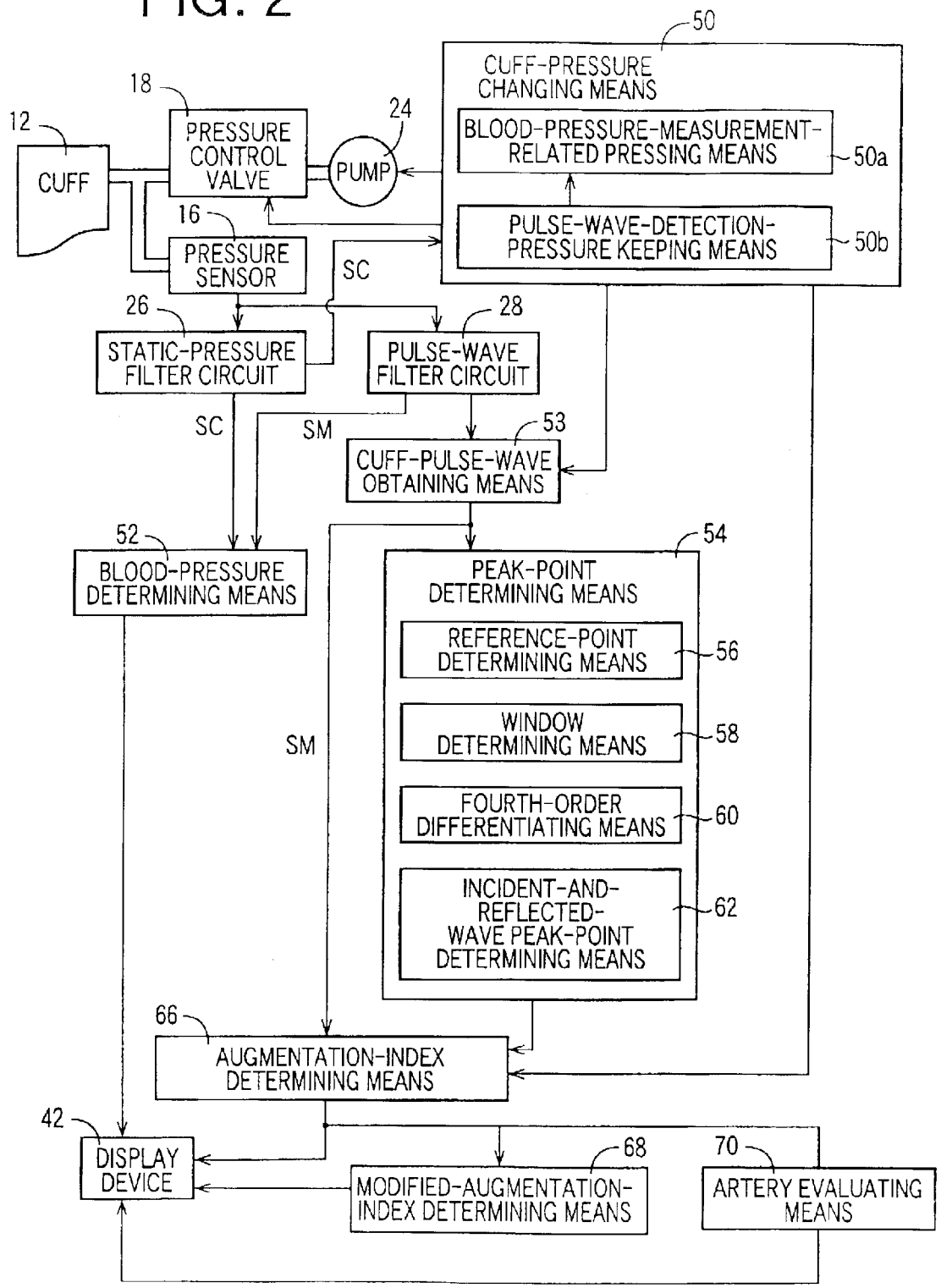
FIG. 2 is a block diagram for explaining essential control functions of an electronic control device of the blood-pressure measuring apparatus having the augmentation-index determining function, shown in FIG. 1.

FIG. 2 is a block diagram for explaining essential control functions of the control device 32 of the blood-pressure measuring apparatus 10.

Figure 3:
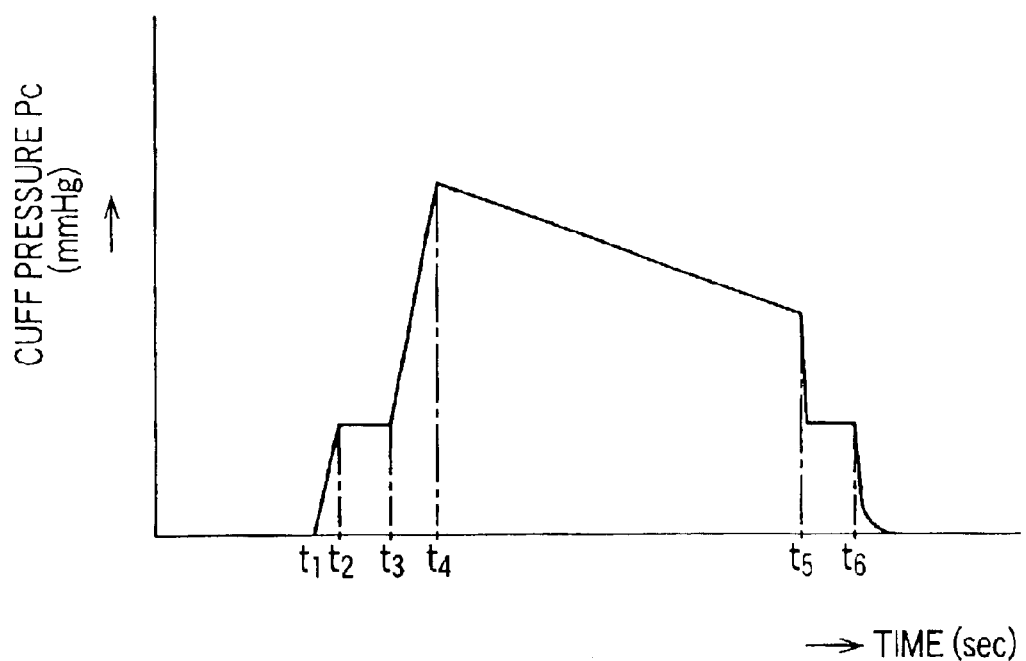
FIG. 3 is a view for explaining change of cuff pressure caused by a cuff-pressure changing means shown in FIG. 2.

A cuff-pressure changing means 50 operates, based on the cuff-pressure signal SC supplied from the static-pressure filter circuit 26, the pressure control valve 18 and the air pump 24 so as to change the cuff pressure Pc. Thus, the static-pressure filter circuit 26, the pressure control valve 18, the air pump 24, and the cuff-pressure changing means 50 cooperate with one another to provide a cuff-pressure changing device. The cuff-pressure changing means 50 includes a blood-pressure-measurement-related pressing means 50a for pressing, in a blood-pressure measurement, the upper arm 14 with the cuff 12 being wound, i.e., with a pressure sufficiently higher than a pulse-wave detection pressure, e.g., a pressure higher than a systolic blood pressure $BP_{SYS}$ of the subject; and a pulse-wave-detection-pressure keeping means 50b for keeping, in each of an initial portion and a terminal portion of a pressing period in which the blood-pressure-measurement-related pressing means 50a presses the arm 14 with the cuff 12 for the blood-pressure measurement, the pressure of the cuff 12 to the pulse-wave detection pressure pre-determined to be lower than a diastolic blood pressure $BP_{DIA}$ of the subject, so as to obtain the cuff-pulse-wave signal SC to be used to determine an augmentation index AI. More specifically described, as shown in FIG. 3, in the initial portion of the pressing period, the cuff-pressure changing means 50 keeps, for a time corresponding to not less than one heartbeat of the subject, the cuff pressure Pc to the pre-determined pulse-wave detection pressure lower than the diastolic blood pressure $BP_{DIA}$ of the subject, subsequently quickly increases the cuff pressure Pc from the pulse-wave detection pressure to a target pressure value (e.g., 180 mmHg) pre-determined to be higher than the systolic blood pressure $BP_{SYS}$ of the subject, and then slowly decreases the cuff pressure Pc at a pre-scribed rate of from 2 to 3 mmHg/sec. In addition, in the terminal portion of the pressing period after a blood-pressure determining means 52, described later, determines a diastolic blood pressure $BP_{DIA}$ of the subject, the cuff-pressure changing means 50 keeps, for a time corresponding to not less than one heartbeat of the subject, the cuff pressure Pc to the pre-determined pulse-wave detection pressure lower than the diastolic blood pressure $BP_{DIA}$ of the subject, so as to obtain another cuff pulse wave, and then releases the cuff pressure Pc. If the above-indicated pulse-wave detection pressure is higher than a diastolic blood pressure $BP_{DIA}$ of the subject, the cuff pulse wave extracted by the pulse-wave filter circuit 28 is deformed. In particular, if pulse-wave detection pressure is higher than a mean blood pressure $BP_{MEAN}$ of the subject, the cuff pulse wave is so largely deformed that an accurate augmentation index AI cannot be determined. Thus, the pulse-wave detection pressure is preferably lower than a mean blood pressure $BP_{MEAN}$ of the subject, more preferably lower than a diastolic blood pressure $BP_{DIA}$ of the subject, for example, a pressure of from 40 mmHg to 60 mmHg. However, if the cuff pressure Pc is too low, the cuff pulse wave detected is too small to determine an accurate augmentation index AI. Thus, the pulse-wave detection pressure is pre-determined at a value that assures that a cuff pulse wave having a sufficiently great magnitude is detected.

The blood-pressure determining means 52 determines, based on the cuff-pressure signal SC continuously obtained, and the change of respective amplitudes of a plurality of heartbeat-synchronous pulses of the cuff-pulse-wave signal SM continuously obtained, each during the slow decreasing of the cuff pressure Pc under the control of the cuff-pressure changing means 50, a systolic blood pressure $BP_{SYS}$, a mean blood pressure $BP_{MEAN}$ and a diastolic blood pressure $BP_{DIA}$ of the subject, according to well-known oscillometric method. In addition, the determining means 52 operates the display device 42 to display the thus determined systolic blood pressure $BP_{SYS}$, etc. A cuff-pulse-wave obtaining means 53 obtains, before the pressing of the cuff 12 for the blood-pressure measurement, i.e., the pressing of the blood-pressure-measurement-related pressing means 50a, and in the state in which the cuff pressure Pc is kept at the pulse-wave detection pressure by the pulse-wave-detection-pressure keeping means 50b, a length of the cuff-pulse-wave signal SM that corresponds to at least one heartbeat of the subject, for the purpose of determining an augmentation index AI.

Figure 4:
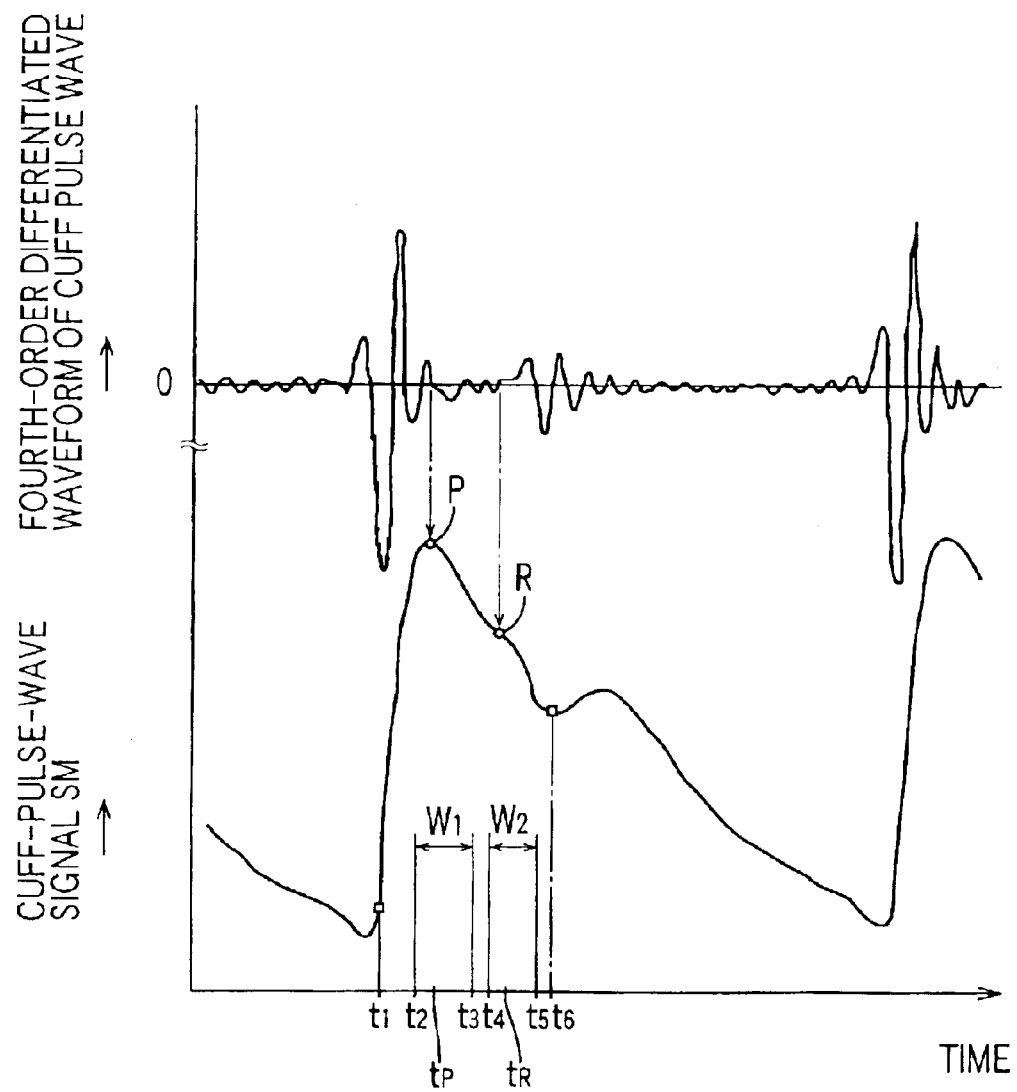
FIG. 4 is a time chart showing a relationship among a cuff pulse wave, a fourth-order-differentiated waveform, a rising-point window $W_1$, a notch-point window $W_2$, an incident-wave peak point P, and a reflected-wave peak point R that are obtained or determined by the control device shown in FIG. 2.
Figure 5:
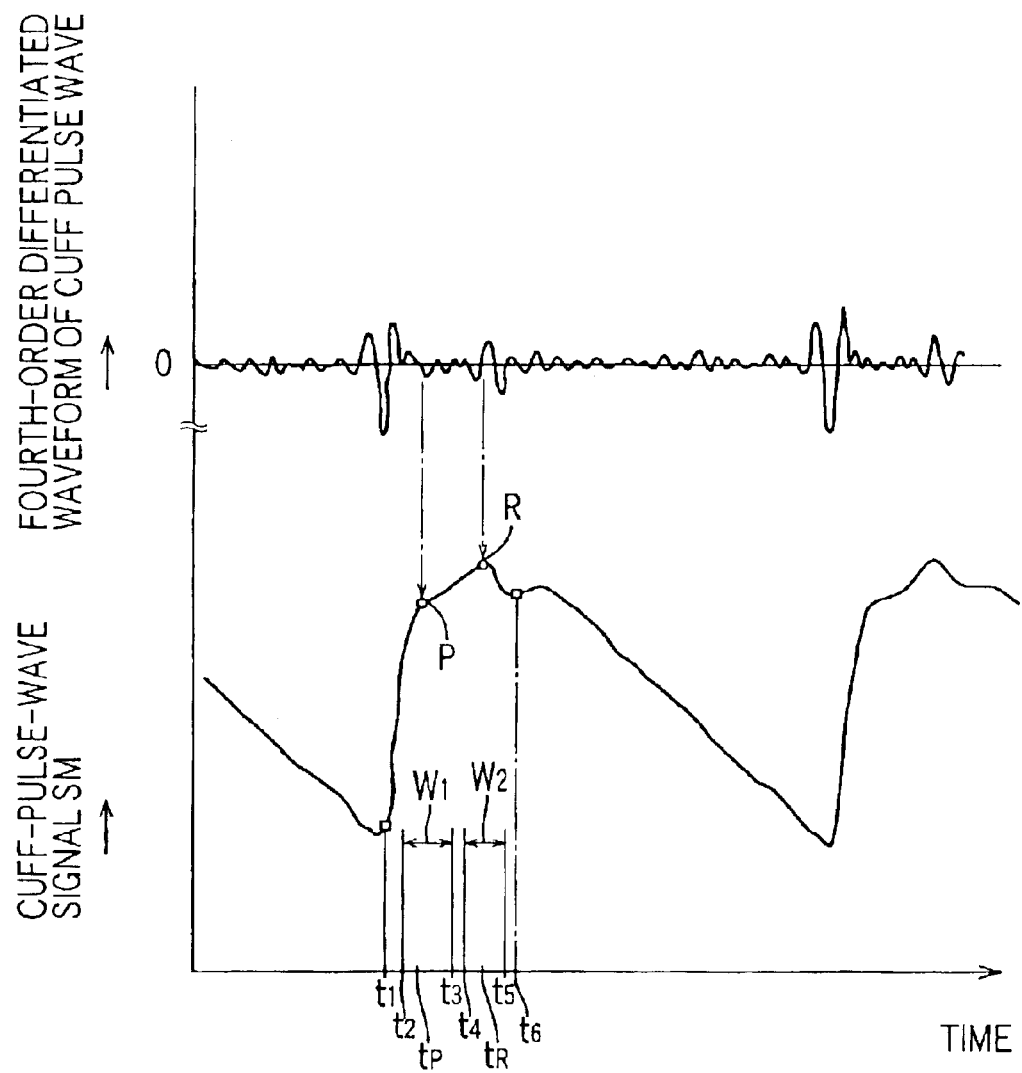
FIG. 5 is a time chart showing a relationship among a cuff pulse wave having a different waveform than that of the cuff pulse wave shown in FIG. 3, a fourth-order-differentiated waveform, a rising-point window $W_1$, a notch-point window $W_2$, an incident-wave peak point P, and a reflected-wave peak point R.

A peak-point determining means 54 subjects, to fourth-order differentiation (i.e., four-time differentiations), the cuff-pulse-wave signal SM obtained from the cuff 12 by the cuff-pulse-wave obtaining means 53 in the state in which the cuff pressure Pc is kept at the pulse-wave detection pressure in each of the initial and terminal portions of the pressing period, and determines, based on the thus obtained fourth-order-differentiated waveform of the signal SM, more specifically, zero-crossing points of the differentiated waveform, a peak point P of an incident-wave component of the signal SM, a time $t_P$ of occurrence of the point P, a peak point R of a reflected-wave component of the signal SM, and a time $t_R$ of occurrence of the point R. FIGS. 4 and 5 show two cuff-pulse-wave signals SM having different waveforms, respectively, and their respective fourth-order-differentiated waveforms, and each of the FIGS. 4 and 5 shows the corresponding one signal SM and its differentiated waveform along a common time axis, and a peak point P of an incident-wave component of the signal SM, a time $t_P$ of occurrence of the point P, a peak point R of a reflected-wave component of the signal SM, and a time $t_R$ of occurrence of the point R.

The peak-point determining means 54 includes a reference-point determining means 56 for determining, based on each of the respective forms of the two cuff pulse waves obtained by the cuff-pulse-wave obtaining means 53, reference points on the each cuff pulse wave, i.e., a rising point $t_1$ and a notch point $t_6$; a window determining means 58 for determining a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$; a fourth-order differentiating means 60 for fourth-order differentiating, i.e., four times differentiating the each cuff pulse wave obtained by the cuff-pulse-wave obtaining means 53; and an incident-and-reflected-wave peak-point determining means 62 for determining, based on two zero-crossing points of the thus obtained fourth-order differentiated waveform that fall within the rising-point window $W_1$ and the notch-point window $W_2$, respectively, a peak point P of an incident-wave component of the cuff pulse wave, a time of occurrence of the peak point P, a peak point R of a reflected-wave component of the cuff pulse wave, and a time $t_R$ of occurrence of the point R. The reference-point determining means 56 determines, as a rising point $t_1$, a point that is subsequent to a local minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as a notch point $t_6$, the first local minimum point, or the first inflection point, subsequent to the maximum point. The incident-and-reflected-wave peak-point determining means 62 determines, as a peak point $t_P$ of an incident-wave component, a zero-crossing point that has a pre-determined position as counted from the start point of the rising-point window $W_1$, e.g., the first zero-crossing point falling in the rising-point window $W_1$, and crosses zero in a direction from a positive area to a negative area; and additionally determines, as a peak point $t_R$ of a reflected-wave component, a zero-crossing point that has a pre-determined position as counted from the start point of the notch-point window $W_2$, e.g., the first zero-crossing point falling in the notch-point window $W_2$, and crosses zero in a direction from the negative area to the positive area. The respective times from the rising point $t_1$ to the start and end points of the rising-point window $W_1$ and the respective times from the notch point $t_6$ to the start and end points of the notch-point window $W_2$, employed by the window determining means 58, are experimentally determined in advance so that the peak points $t_P$, $t_R$ can fall in the widows $W_1$, $W_2$, respectively.

An augmentation-index determining means 66 first determines a maximum magnitude and a minimum magnitude of a heartbeat-synchronous pulse of each of the cuff pulse waves obtained from the cuff 12 kept at the pulse-wave detection pressure in each of the initial and terminal portions of the pressing period, and additionally determines, as a pulse pressure (i.e., a maximum amplitude) PP of the each pulse wave, a difference between the maximum and minimum magnitudes. Moreover, the augmentation-index determining means 66 determines, according to a relationship represented by the following Expression 1, an augmentation index $AI_1$, $AI_2$ based on the pulse pressure PP and a difference $\Delta P$ (=b−a) obtained by subtracting a magnitude, a, of the each cuff pulse wave at the time of occurrence of peak point $t_P$ of the incident-wave component from a magnitude, b, of the each cuff pulse wave at the time of occurrence of peak point $t_R$ of the reflected-wave component, and operates the display device 42 to display the thus determined augmentation indexes $AI_1$, $AI_2$. A modified-augmentation-index determining means 68 determines, based on the respective augmentation indexes $AI_1$, $AI_2$ determined from the respective cuff pulse waves obtained in the initial and terminal portions of the pressing period, a modified augmentation index AI, and operates the display device 42 to display the thus determined modified augmentation index AI. For example, the modified augmentation index AI may be determined as an average of the two augmentation indexes $AI_1$, $AI_2$, so as to reduce the influences caused by the change of respective thickness of skin and subcutaneous tissue of the upper arm 14 pressed by the cuff 12.

$$AI=(\Delta P/PP)\times 100(\%) \quad \text{(Expression 1)}$$

An artery evaluating means 70 evaluates arteriosclerosis or vascular endothelium of the subject based on the respective cuff pulse waves obtained in the initial and terminal portions of the pressing period, or the respective augmentation indexes $AI_1$, $AI_2$ determined by the augmentation-index determining means 66. For example, the artery evaluating means 70 compares the respective shapes or forms of the respective cuff-pulse-wave signals SM obtained in the initial and terminal portions of the pressing period, or the respective augmentation indexes $AI_1$, $AI_2$ determined based on the respective signals SM, and evaluates a degree of softness of arteries of the subject based on a difference of respective amplitudes of the two cuff pulse waves, a difference of respective areas of the two cuff pulse waves, or a difference of the two augmentation indexes. In addition, the artery evaluating means 70 operates the display device 42 to display the evaluated degree of softness of arteries. In this case, as the amplitude difference of the two cuff pulse waves, the area difference of the two cuff pulse waves, or the difference of the two augmentation indexes increases, the degree of softness of arteries increases; and as the amplitude difference, the area difference or the augmentation-index difference decreases, the degree of arteriosclerosis or the degree of hardness of vascular endothelium increases.

Figure 6:
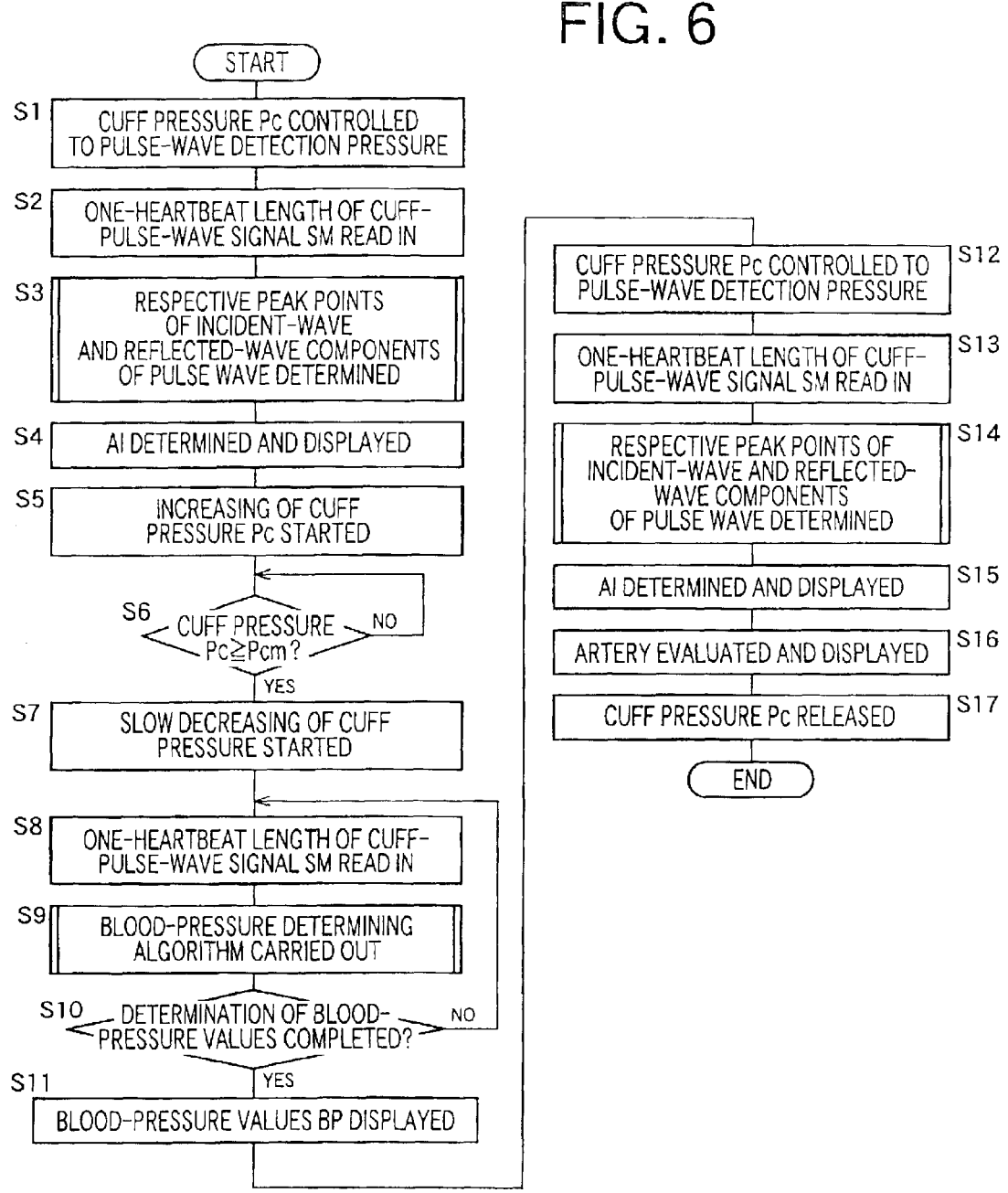
FIG. 6 is a flow chart for explaining the essential control functions of the control device of the blood-pressure measuring apparatus having the augmentation-index determining function, shown in FIG. 1.
Figure 7:
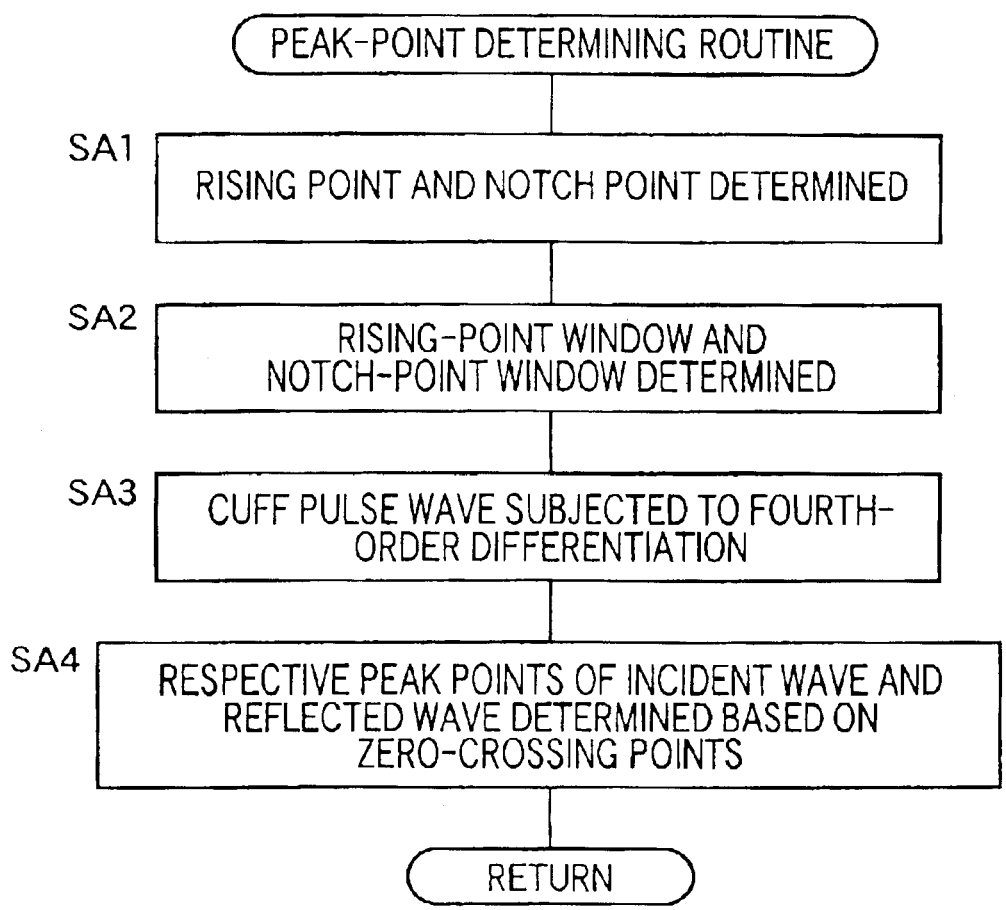
FIG. 7 is a flow chart for explaining a peak-point determining routine employed in the flow chart shown in FIG. 6.

FIG. 6 is a flow chart representing the control functions of the CPU 36, shown in the block diagram of FIG. 2; and FIG. 7 is a flow chart representing a sub-routine corresponding to an incident-and-reflected-wave peak-point determining operation carried out according to FIG. 6.

In FIG. 6, when a measurement starting operation, not shown, is carried out, the control of the CPU starts with Step S1 (hereinafter, the term "Step" is omitted) corresponding to the pulse-wave-detection-pressure keeping means 50b. At S1, the CPU starts the air pump 24 and the pressure control valve 18, and keeps the pressure in the cuff 12 wound around the upper arm 14, to the pulse-wave detection pressure. Subsequently, the control goes to S2 corresponding to the cuff-pulse-wave obtaining means 53. At S2, the CPU reads in a length of the cuff-pulse-wave signal SM that corresponds to at least one heartbeat of the subject. Then, the control goes to S3 corresponding to the peak-point determining means 54. At S3, the CPU carries out the peak-point determining routine shown in FIG. 7.

In FIG. 7, the control of the CPU starts with SA1 corresponding to the reference-point determining means 56. At SA1, the CPU determines, based on the waveform of the cuff pulse wave represented by the cuff-pulse-wave signal SM obtained from the cuff 12 the pressure of which is kept at the pulse-wave detection pressure, reference points on the cuff pulse wave, i.e., a rising point $t_1$ and a notch point $t_6$. For example, the reference-point determining means 56 determines, as the rising point $t_1$, a point that is subsequent to a minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as the notch point $t_6$, the first local minimum point, or the first inflection point, subsequent to the maximum point. Subsequently, the control goes to SA2 corresponding to the window determining means 58. At SA2, the CPU determines a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$. Subsequently, the control goes to SA3 corresponding to the fourth-order differentiating means 60. At SA3, the CPU subjects, to fourth-order differentiation, the cuff-pulse-wave signal SM obtained from the cuff 12 the pressure of which is kept at the pulse-wave detection pressure. Then, the control goes to SA4 corresponding to the incident-and-reflected-wave peak-point determining means 62. At SA4, the CPU determines, based on two zero-crossing points of the thus obtained fourth-order differentiated waveform that fall within the rising-point window $W_1$ and the notch-point window $W_2$, respectively, a peak point P of an incident-wave component of the cuff-pulse-wave signal SM, a time $t_P$ of occurrence of the point P, a peak point R of a reflected-wave component of the signal SM, and a time $t_R$ of occurrence of the point R.

Back to FIG. 6, after the peak point P of the incident-wave component of the cuff-pulse-wave signal SM, the time $t_P$ of occurrence of the point P, the peak point R of the reflected-wave component of the signal SM, and the time $t_R$ of occurrence of the point R are thus determined, the control goes to S4 corresponding to the augmentation-index determining means 66. At S4, the CPU first determines a pulse pressure (a maximum amplitude) PP of the cuff-pulse-wave signal SM obtained from the cuff 12 the pressure of which is kept at the pulse-wave detection pressure, and then determines a difference $\Delta P$ (=b−a) by subtracting a magnitude, a, of the cuff-pulse-wave signal SM at the time of occurrence of peak point $t_P$ of the incident-wave component from a magnitude, b, of the signal SM at the time of occurrence of peak point $t_R$ of the reflected-wave component. Moreover, the CPU determines, according to the relationship represented by the above-indicated Expression 1, an augmentation index $AI_1$ based on the pulse pressure PP and the difference $\Delta P$, and operates the display device 42 to display the thus determined augmentation index $AI_1$.

After the augmentation index $AI_1$ is thus determined based on the cuff pulse wave obtained in the initial portion of the pressing period in which the cuff 12 presses the upper arm 14 in the blood-pressure measurement, the control goes to Steps S5 to S11, for carrying out a blood pressure measurement. More specifically described, at S5, the CPU starts quick increasing of the cuff pressure Pc from the pulse-wave detection pressure to the target pressure value Pcm (e.g., 180 mmHg) determined in advance to be higher than a systolic blood pressure $BP_{SYS}$ of the upper arm of the subject. Then, the control goes to S6 to judge whether the cuff pressure Pc is higher than the target pressure Pcm. S6 is repeated until a positive judgment is made, while the cuff pressure Pc is quickly increased. Meanwhile, if a positive judgment is made at S6, the control goes to S7 to stop the air pump 24 and operate the pressure control valve 18 to slowly decrease the cuff pressure Pc at a low rate of from 3 to 5 mmHg/sec. Thus, S5 to S7 correspond to the blood-pressure-measurement-related pressing means 50a.

Then, at S8, the CPU reads in respective one-heartbeat lengths of the cuff-pulse-wave signal SM supplied from the pulse-wave filter circuit 28 and the cuff-pressure signal SC. Subsequently, the control goes to S9 corresponding to the blood-pressure determining means 52. At S9, the CPU determines, based on change of respective amplitudes of a plurality of heartbeat-synchronous pulses of the cuff pulse wave represented by the cuff-pulse-wave signal SM, and respective values of the cuff pressure Pc represented by the cuff-pressure signal SC, each obtained at S5 during the slow decreasing of the cuff pressure Pc, a systolic blood pressure $BP_{SYS}$, a mean blood pressure $BP_{MEAN}$, and a diastolic blood pressure $BP_{DIA}$ of the subject, according to well-known oscillometric method. Then, at S10, the CPU judges whether all blood-pressure values BP have been determined at S5. S9 is repeated until a positive judgment is made, while the current blood-pressure measuring operation is continued. Meanwhile, if a positive judgment is made at S10, the control goes to S11 to operate the display device 42 to display the thus determined systolic blood pressure $BP_{SYS}$, mean blood pressure $BP_{MEAN}$, and diastolic blood pressure $BP_{DIA}$ of the subject, determined at S8.

After the blood-pressure values has been determined as described above, the control goes to S12 corresponding to the pulse-wave-detection-pressure keeping means 50b. At S12, the CPU operates the air pump 24 and the pressure control valve 18 to keep the pressure of the cuff 12 wound around the upper arm 14 again to the pulse-wave detection pressure. Subsequently, the control goes to S13 corresponding to the cuff-pulse-wave obtaining means 53. At S13, the CPU reads in a length of the cuff-pulse-wave signal SM that corresponds to at least one heartbeat of the subject. Then, the control goes to S14 corresponding to the peak-point determining means 54. At S14, the CPU carries out the peak-point determining routine shown in FIG. 7, and determines a peak point P of an incident-wave component of the cuff-pulse-wave signal SM, a time of occurrence of the peak point P, a peak point R of a reflected-wave component of the signal SM, and a time of occurrence of the peak point R. Then, the control goes to S15 corresponding to the augmentation-index determining means 66 and the modified-augmentation-index determining means 68. At S15, the CPU first determines a pulse pressure (i.e., a maximum amplitude) PP of the cuff-pulse-wave signal SM obtained from the cuff 12 the pressure of which is kept at the pulse-wave detection pressure, and then determines a difference $\Delta P$ (=b−a) by subtracting a magnitude, a, of the cuff-pulse-wave signal SM at the time of occurrence of peak point $t_P$ of the incident-wave component from a magnitude, b, of the signal SM at the time of occurrence of peak point $t_R$ of the reflected-wave component. Moreover, the CPU determines, according to the relationship represented by the above-indicated Expression 1, an augmentation index $AI_2$ based on the pulse pressure PP and the difference $\Delta P$, and operates the display device 42 to display the thus determined augmentation index $AI_2$. In addition, the CPU determines, based on the respective augmentation indexes $AI_1$, $AI_2$ determined from the respective cuff pulse waves obtained in the initial and terminal portions of the pressing period, a modified augmentation index AI that is freed from the influences caused by the deformation of skin and subcutaneous tissue of the upper arm 14 pressed by the cuff 12. The CPU operates the display device 42 to display the thus determined modified augmentation index AI.

Then, the control proceeds with S16 corresponding to the artery evaluating means 70. At S16, the CPU evaluates arteriosclerosis or vascular endothelium of the subject based on the respective shapes of the respective cuff pulse waves obtained in the initial and terminal portions of the pressing period, or the respective augmentation indexes $AI_1$, $AI_2$ determined based on the respective cuff pulse waves. For example, the CPU compares the respective shapes of the respective cuff-pulse-wave signals SM, or the respective augmentation indexes $AI_1$, $AI_2$, with each other, and evaluates a degree of softness of arteries of the subject based on a difference of respective amplitudes of the two cuff pulse waves, a difference of respective areas of the two cuff pulse waves, or a difference of the two augmentation indexes. In addition, the CPU operates the display device 42 to display the evaluated degree of softness of arteries. In this case, as the amplitude difference of the two cuff pulse waves, the area difference of the two cuff pulse waves, or the difference of the two augmentation indexes increases, the degree of softness of arteries increases; and as the amplitude difference, the area difference or the augmentation-index difference decreases, the degree of arteriosclerosis or the degree of hardness of vascular endothelium increases. Finally, at S17, the CPU operates for releasing the cuff pressure Pc and thereby decreasing the cuff pressure down to atmospheric pressure.

As is apparent from the foregoing description of the present embodiment, the cuff-pulse-wave obtaining means 53 (S2, S13) obtains, during the pressing period in which the cuff presses the upper arm in the blood pressure measurement, the cuff pulse wave to be used to determine the augmentation index AI. Therefore, the pressing period in which the cuff presses the portion of the subject for measuring the augmentation index and the blood pressure can be advantageously shortened.

Also, in the present embodiment, the pulse-wave-detection-pressure keeping means 50b (S1, S12) keeps the cuff pressure to the pre-determined pulse-wave detection pressure, and the cuff-pulse-wave obtaining means 53 (S2, S13) obtains, in the state in which the cuff pressure is kept, by the pulse-wave-detection-pressure keeping means 50b, to the pre-determined pulse-wave detection pressure, the cuff-pulse-wave signal SM as the pressure oscillation occurring to the cuff. Therefore, the cuff-pulse-wave signal SM is freed from deformation caused by changing of the cuff pressure Pc, and the augmentation index AI is accurately determined based on the cuff-pulse-wave signal SM.

Also, in the present embodiment, the pulse-wave-detection-pressure keeping means 50b (S1, S12) keeps the pressure of the cuff 12 to the pre-determined pulse-wave detection pressure, in each of the initial portion and the terminal portion of the pressing period, and the cuff-pulse-wave obtaining means 53 (S2, S13) obtains a portion of the cuff-pulse-wave signal SM representing a pressure oscillation occurring to the cuff in a state in which the pressure of the cuff 12 is kept at the pre-determined pulse-wave detection pressure in the initial portion of the pressing period, and obtains another portion of the cuff-pulse-wave signal SM representing a pressure oscillation occurring to the cuff in a state in which the pressure of the cuff 12 is kept at the pre-determined pulse-wave detection pressure in the terminal portion of the pressing period, and the augmentation-index determining means 66 (S4, S15) determines respective augmentation indexes $AI_1$, $AI_2$ of the subject based on the respective portions of the cuff-pulse-wave signal SM obtained by the cuff-pulse-wave obtaining means 53 in the initial and terminal portions of the pressing period. Thus, the respective augmentation indexes $AI_1$, $AI_2$ of the subject are obtained based on the respective cuff pulse waves obtained in the initial and terminal portions of the pressing period in which the cuff presses the upper arm 14 in the blood-pressure measurement.

Also, in the present embodiment, the modified-augmentation-index determining means 68 (S15) determines the modified augmentation index AI based on the respective augmentation indexes $AI_1$, $AI_2$ determined by the augmentation-index determining means 66 (S4, S15) from the respective cuff pulse waves obtained in the initial and terminal portions of the pressing period in which the cuff 12 presses the upper arm 14. Thus, the modified augmentation index AI freed from influences caused by the deformation of skin and subcutaneous tissue of the subject's portion that contains a lot of water and is pressed by the cuff, can be obtained.

Also, in the present embodiment, the artery evaluating means 70 (S16) evaluates the degree of arteriosclerosis or the vascular endothelium of the subject based the respective cuff pulse waves obtained in the initial and terminal portions of the period of pressing of the cuff 12 for the blood-pressure measurement, or the respective augmentation indexes $AI_1$, $AI_2$ determined based on the respective cuff pulse waves by the augmentation-index determining means 66 (S4, S15). For example, the artery evaluating means compares the respective cuff pulse waves obtained in the initial and terminal portions of the pressing period, or the respective augmentation indexes, with each other, and evaluates a degree of softness of arteries of the subject based on a difference of respective amplitudes of the two cuff pulse waves, a difference of respective areas of the two cuff pulse waves, or a difference of the two augmentation indexes. In this case, as the amplitude difference of the two cuff pulse waves, the area difference of the two cuff pulse waves, or the difference of the two augmentation indexes increases, the degree of softness of arteries increases; and as the amplitude difference, the area difference or the augmentation-index difference decreases, the degree of arteriosclerosis or the degree of hardness of vascular endothelium increases.

Also, in the present embodiment, the pulse-wave-detection-pressure keeping means 50b keeps the cuff pressure to the pulse-wave detection pressure lower than the diastolic blood pressure of the subject, e.g., pressure of from 40 to 60 mmHg. Thus, the cuff-pulse-wave signal SM obtained is free from deformation caused by the tensile force of the cuff 12. Accordingly, the augmentation index determined based on the cuff pulse wave enjoys a high accuracy.

Also, in the present embodiment, the blood-pressure measuring apparatus 10 having the augmentation-index determining function can be used as an arteriosclerosis inspecting apparatus. In this case, the arteriosclerosis inspecting apparatus inspects a degree of arteriosclerosis of a living subject based on an augmentation index AI determined by the augmentation-index determining means 66.

Also, in the present embodiment, the peak-point determining means 54 (S3, S14) determines, based on the fourth-order differentiated waveform of the cuff-pulse-wave signal SM, provided by the fourth-order differentiating means 60 (SA3), the respective peak points P, R of the incident-wave and reflected-wave components of the signal SM; and the augmentation-index determining means 66 (S4, S15) accurately determines, as the augmentation index AI, the proportion of the difference ΔP between the amplitude of the cuff pulse wave at the thus determined peak point P of the incident-wave component and the amplitude of the cuff pulse wave at the thus determined peak point R of the reflected-wave component, to the pulse pressure PP.

Also, in the present embodiment, the reference-point determining means 56 (SA1) determines the rising point of the cuff-pulse-wave signal SM, and the window determining means 58 (SA2) determines the rising-point window $W_1$ based on the rising point of the cuff-pulse-wave signal SM determined by the reference-point determining means 56. In addition, the peak-point determining means 54 determines, based on the zero-crossing point of the fourth-order differentiated waveform that falls in the rising-point window $W_1$, the peak point P of the incident-wave component. Thus, as compared with a case in which a peak point is determined on a moderate waveform, the peak point P of the incident-wave component is more accurately determined and accordingly the augmentation index AI is more accurately determined based on the peak point P.

Also, in the present embodiment, the peak-point determining means 54 selects, as the peak point P of the incident-wave component, one of the zero-crossing points of the fourth-order differentiated waveform that fall in the rising-point window $W_1$, such that the selected one zero-crossing point has prescribed crossing direction and position as seen from the start or end point of the rising-point window $W_1$. Therefore, the peak point P of the incident-wave component is more accurately determined and accordingly the augmentation index AI is more accurately determined based on the peak point P.

Also, in the present embodiment, the reference-point determining means 56 (SA1) determines the notch point of the cuff-pulse-wave signal SM, and the window determining means 58 (SA2) determines the notch-point window $W_2$ based on the notch point of the cuff-pulse-wave signal SM determined by the reference-point determining means 56. In addition, the peak-point determining means 54 determines, based on the zero-crossing point of the fourth-order differentiated waveform that falls in the notch-point window $W_2$, the peak point R of the reflected-wave component. Thus, as compared with a case in which a peak point is determined on a moderate waveform, the peak point R of the reflected-wave component is more accurately determined and accordingly the augmentation index AI is more accurately determined based on the peak point R.

Also, in the present embodiment, the peak-point determining means 54 selects, as the peak point R of the reflected-wave component, one of the zero-crossing points of the fourth-order differentiated waveform that fall in the notch-point window $W_2$, such that the selected one zero-crossing point has prescribed crossing direction and position as seen from the start or end point of the notch-point window $W_2$. Therefore, the peak point R of the reflected-wave component is more accurately determined and accordingly the augmentation index AI is more accurately determined based on the peak point R.

While the present invention has been described in its preferred embodiment by reference to the drawings, it is to be understood that the invention may otherwise be embodied.

For example, in the illustrated blood pressure measuring apparatuses 10 having the augmentation-index determining function, the cuff 12 is worn the upper arm 14. However, the cuff 12 may be worn on a different body portion of the subject, such as a femoral portion or an ankle.

In the illustrated blood pressure measuring apparatuses 10 having the augmentation-index determining function, the cuff pulse wave is obtained in the state in which the cuff pressure Pc is kept at the pre-determined pulse-wave detection pressure. However, a cuff pulse wave may be obtained while the cuff pressure Pc is slowly changed, because a cuff pulse obtained through a high-performance filter is less deformed.

In addition, generally, augmentation index AI is calculated according to the mathematical expression (Expression 1) wherein the denominator is pulse pressure PP. However, even in the case where the denominator is replaced with an amplitude of low-pressure-cuff pulse wave at the time of occurrence of peak point of the incident-wave component or at the time of occurrence of peak point of the reflected-wave component, a value calculated according to the thus modified expression reflects a degree of arteriosclerosis. Therefore, in Expression 1, pulse pressure PP may be replaced with amplitude of low-pressure-cuff pulse wave at the time of occurrence of peak point of the incident-wave component or at the time of occurrence of peak point of the reflected-wave component. In short, augmentation index may be defined as any value that indicates a proportion of a reflected-wave component of a cuff pulse wave to an incident-wave component of the same.

In the illustrated embodiment, the incident-and-reflected-wave peak-point determining means 62 determines, as the peak point P of the incident wave, the first zero-crossing point of the fourth-order differentiated waveform that falls in the rising-point window $W_1$ and where the waveform crosses zero in a direction from a positive area to a negative area, and additionally determines, as the peak point R of the reflected wave, the first zero-crossing point that falls in the notch-point window $W_2$ and where the waveform crosses zero in a direction from the negative area to the positive area. However, the position and direction of each zero crossing may be changed depending upon the manner in which the rising-point window $W_1$ and the notch-point window $W_2$ are determined and the manner in which the fourth-order differentiation is applied to the cuff pulse wave.

In the illustrated embodiment, the peak-point determining means 54 determines the peak point P of the incident wave and the peak point R of the reflected wave, based on the zero-crossing points on the fourth-order differentiated waveform of the cuff-pulse-wave signal SM. However, respective peak points of an incident wave and a reflected wave may be determined on a cuff-pulse-wave signal SM obtained in a state in which the pre-determined pulse-wave detection pressure is higher than a systolic blood pressure $BP_{SYS}$ of a living subject.

It is to be understood that the present invention may be embodied with other changes, improvements, and modifications that may occur to a person skilled in the art without departing from the spirit and scope of the invention.

What is claimed is:

1. A blood-pressure measuring apparatus comprising:
    a cuff which is adapted to be worn on a portion of a living subject to press said portion;
    an augmentation-index determining means for determining an augmentation index of the subject based on a cuff pulse wave obtained from the cuff; and
    a cuff-pulse-wave obtaining means for obtaining, during a pressing period in which the cuff presses said portion of the subject for measuring a blood pressure of the subject, the cuff pulse wave from the cuff so that the augmentation-index determining means determines the augmentation index based on the obtained cuff pulse wave.

2. An apparatus according to claim 1, further comprising a pulse-wave-detection-pressure keeping means for keeping a pressure in the cuff to a pre-determined pulse-wave detection pressure,
    wherein the cuff-pulse-wave obtaining means obtains, as the cuff pulse wave, a pressure oscillation occurring to the cuff in a state in which the pressure in the cuff is kept at the pre-determined pulse-wave detection pressure.

3. An apparatus according to claim 2, wherein the pulse-wave-detection-pressure keeping means keeps the pressure in the cuff to the pre-determined pulse-wave detection pressure, in each of an initial portion and a terminal portion of the pressing period,
    wherein the cuff-pulse-wave obtaining means obtains, as a first cuff pulse wave, a pressure oscillation occurring to the cuff in a state in which the pressure in the cuff is kept at the pre-determined pulse-wave detection pressure in the initial portion of the pressing period, and obtains, as a second cuff pulse wave, a pressure oscillation occurring to the cuff in a state in which the pressure in the cuff is kept at the pre-determined pulse-wave detection pressure in the terminal portion of the pressing period, and wherein the augmentation-index determining means determines a first augmentation index of the subject based on the first cuff pulse wave obtained from the cuff in the initial portion of the pressing period, and determines a second augmentation index of the subject based on the second cuff pulse wave obtained from the cuff in the terminal portion of the pressing period.

4. An apparatus according to claim 3, further comprising a modified-augmentation-index determining means for determining a modified augmentation index based on the first and second augmentation indexes determined by the augmentation-index determining means.

5. An apparatus according to claim 3, further comprising an artery evaluating means for evaluating a degree of arteriosclerosis or a vascular endothelium of the subject based on the first and second augmentation indexes determined by the augmentation-index determining means.

* * * * *